(12) United States Patent
Roorda et al.

(10) Patent No.: US 10,022,127 B2
(45) Date of Patent: Jul. 17, 2018

(54) DOUBLE BELLOW OCCLUDER FOR SCLEROTHERAPY

(75) Inventors: Wouter Erik Roorda, Palo Alto, CA (US); Michael Green, Pleasanton, CA (US); Neil Burkhart, Fremont, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 1393 days.

(21) Appl. No.: 13/287,215

(22) Filed: Nov. 2, 2011

(65) Prior Publication Data
US 2013/0110081 A1  May 2, 2013

(51) Int. Cl.
*A61M 25/00* (2006.01)
*A61B 17/12* (2006.01)
*A61M 25/10* (2013.01)

(52) U.S. Cl.
CPC .. *A61B 17/12022* (2013.01); *A61B 17/12186* (2013.01); *A61M 25/00* (2013.01); *A61B 17/12136* (2013.01); *A61B 2017/12004* (2013.01); *A61B 2017/1205* (2013.01); *A61B 2218/002* (2013.01); *A61B 2218/007* (2013.01); *A61M 25/1011* (2013.01); *A61M 2025/0004* (2013.01); *A61M 2025/1052* (2013.01)

(58) Field of Classification Search
CPC ...... A61M 25/1011; A61M 2025/1013; A61M 2025/1015; A61M 2025/1065; A61M 2025/1068
See application file for complete search history.

(56) References Cited

U.S. PATENT DOCUMENTS

| | | | | |
|---|---|---|---|---|
| 3,810,474 A | * | 5/1974 | Cross | A61M 16/04 128/207.15 |
| 3,996,938 A | * | 12/1976 | Clark, III | A61B 17/221 606/192 |
| 4,024,873 A | * | 5/1977 | Antoshkiw | A61B 5/028 604/101.04 |
| 4,696,304 A | * | 9/1987 | Chin | A61B 5/028 600/486 |
| 4,921,484 A | * | 5/1990 | Hillstead | A61M 25/10 604/104 |
| 5,466,222 A | * | 11/1995 | Ressemann | A61M 25/104 604/103.09 |

(Continued)

*Primary Examiner* — Kami A Bosworth
*Assistant Examiner* — William Carpenter
(74) *Attorney, Agent, or Firm* — Womble Bond Dickinson (US) LLP

(57) ABSTRACT

The disclosed subject matter describes systems and methods of delivering a therapeutic agent, such as a sclerosing agent, to the walls of a blood vessel to perform sclerotherapy. In an exemplary embodiment a catheter includes a guidewire catheter having at least one guidewire lumen extending therethrough and a slidable concentric tube disposed over the guidewire catheter. At least one bellow is coupled to the concentric tube and configured for conversion between an unexpanded and expanded configuration wherein movement of the concentric tube in a first direction causes the at least one bellow to expand and movement of the concentric tube in a second direction causes the at least one bellow to contract. Additionally, the concentric tube contains at least one port for delivery of a therapeutic agent, e.g. a sclerosing agent. The at least one bellow expands and contracts via mechanical forces.

11 Claims, 3 Drawing Sheets

(56) References Cited

U.S. PATENT DOCUMENTS

| | | | |
|---|---|---|---|
| 5,487,730 A * | 1/1996 | Marcadis | A61M 25/04 |
| | | | 604/103.07 |
| 5,665,063 A | 9/1997 | Roth | |
| 5,766,192 A * | 6/1998 | Zacca | A61B 17/320725 |
| | | | 606/159 |
| 5,827,304 A * | 10/1998 | Hart | A61B 17/22031 |
| | | | 600/571 |
| 6,165,196 A | 12/2000 | Stack | |
| 6,231,588 B1 * | 5/2001 | Zadno-Azizi | A61B 17/12022 |
| | | | 604/99.02 |
| 6,508,777 B1 | 1/2003 | Macoviak | |
| 6,997,898 B2 * | 2/2006 | Forman | A61M 25/1011 |
| | | | 604/101.03 |
| 7,060,051 B2 | 6/2006 | Palasis | |
| 7,077,836 B2 | 7/2006 | Lary | |
| 7,181,290 B2 * | 2/2007 | Chitre | A61N 1/056 |
| | | | 600/585 |
| 2004/0143240 A1 * | 7/2004 | Armstrong | A61M 25/00 |
| | | | 604/528 |
| 2006/0064059 A1 * | 3/2006 | Gelfand | A61B 5/02028 |
| | | | 604/103.06 |
| 2009/0270801 A1 * | 10/2009 | Shimada | A61M 25/0023 |
| | | | 604/96.01 |
| 2010/0137793 A1 * | 6/2010 | Hirszowicz | A61M 25/1002 |
| | | | 604/96.01 |

* cited by examiner

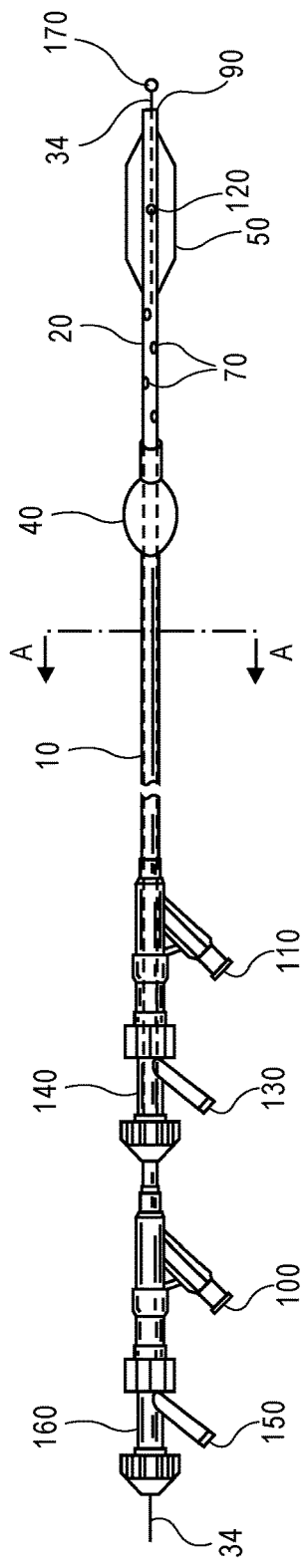
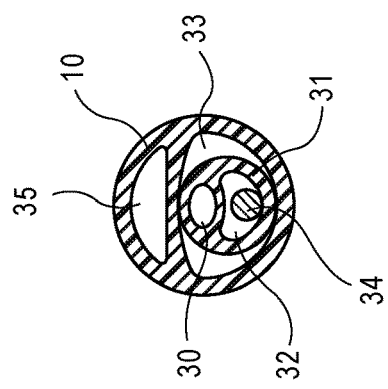
FIG. 1 (PRIOR ART)
FIG. 2 (PRIOR ART)

DOUBLE BELLOW OCCLUDER FOR SCLEROTHERAPY

FIELD OF THE DISCLOSED SUBJECT MATTER

The disclosed subject matter relates to treating blood vessels using a therapeutic agent. More particularly, the disclosed subject matter relates to a medical device configured to deliver an agent at select locations within a patient's blood vessel. An exemplary embodiment of such a device includes a catheter having a slidable concentric tube disposed thereon with a plurality of bellows coupled thereto for expansion/contraction to occlude a vessel for delivery of a therapeutic agent, such as a sclerosing agent, to the walls of a blood vessel to perform sclerotherapy.

BACKGROUND OF THE DISCLOSED SUBJECT MATTER

Varicose veins are blood vessels that have become enlarged and tortuous over a period of time. Most commonly, varicose veins occur in veins on the leg, although they can occur elsewhere. Varicose veins are caused when the leaflets of the valves in the blood vessel no longer close properly, thereby allowing for retrograde flow and pooling of blood.

Varicose veins are most common in the superficial veins of the legs. They are often painful and can produce ankle swelling, skin discoloration, dermatitis or venous eczema, cramps, and skin tightness around the affected region. In severe cases of varicose veins, complications may occur. For example, the varicose veins may become very painful and hinder a person's ability to work or perform routine motions and exercises. Skin conditions including itching and flaking associated with varicose veins may also predispose a person to skin loss. Development of serious conditions like blood clots, carcinoma, or sarcoma, may also occur.

As a result, many non-surgical and surgical treatments of varicose veins have been developed. Non-surgical treatments include sclerotherapy, elastic stockings, elevating the legs, and exercise. The traditional surgical treatment has been vein stripping to remove the affected veins. Newer surgical treatments include ultrasound-guided foam sclerotherapy, radiofrequency ablation and endovenous laser treatment.

Sclerotherapy is a commonly performed non-surgical treatment for treating varicose veins in which a sclerosing agent is injected into the veins to make them shrink. Complications of sclerotherapy are rare but can include blood clots and ulceration. Furthermore, conventional sclerotherapy techniques often result in incomplete and/or uneven treatment along the length of the patient's blood vessel.

In order for sclerotherapy to be effective, it is necessary to evenly dispense the sclerosing agent throughout the wall of the vein without using toxic levels of the sclerosing agent. This is not particularly difficult for the smaller veins. However, it is quite difficult or nearly impossible in larger veins. When a larger vein is injected with a sclerosing agent, the sclerosing agent is quickly diluted by the large volume of blood in the vein. As a result, the vein is sclerosed only in the region of the injection. If the procedure is continued, and the injections are far apart, the vein can become disfigured. The problem cannot be cured by injecting a more potent solution of sclerosing agent, because the sclerosing agent may become toxic at such a concentration. Therefore, a need exists for a system that is capable of delivering a sclerosing agent to the varicose vein walls that prevents the dilution of the sclerosing agent into the blood.

SUMMARY OF DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a medical device configured for localized delivery a therapeutic agent via a catheter for occluding a blood vessel comprising a slidable concentric tube disposed over the guidewire catheter. At least one bellow is coupled to the concentric tube and configured for conversion between an unexpanded and expanded configuration, wherein movement of the concentric tube in a first, e.g. distal, direction causes the at least one bellow to expand and movement of the concentric tube in a second, e.g. proximal, direction causes the at least one bellow to contract. Preferably, the catheter includes first and second bellows. In some embodiments, the first and second bellows can be components of a plurality of bellows, e.g., three or more. In some embodiments, the catheter comprises a guidewire lumen extending through the length of the catheter. While a guide wire may be preferred by some physicians, it is not required, and the catheter can be made more cost efficiently without a guidewire lumen. The invention contemplates both a catheter with and without a guidewire lumen.

In an exemplary embodiment, bellows are coupled to the concentric tube. In one embodiment the bellows are first and second bellows. The bellows (regardless of how many) can be configured to have independent operating tubes. Thus with first and second bellows, for example, each of the first and second bellows can be operated by its own tube. Thus, the inflation and/or contraction of one bellow can be independent from the inflation and/or contraction of another bellow. Alternatively, the bellows can be configured to work dependently or in unison, if desired. Each of the bellows can be associated with the concentric tube.

Additionally, the concentric tube contains at least one port for delivery of a therapeutic agent, such as a sclerosing agent including ethanol. The therapeutic agent is dispensed in the lumen defined in a space between the concentric tube and the guidewire catheter. Further, the at least one port is disposed between a first and second bellow. Preferably, the at least one bellow expands and contracts solely via mechanical forces.

In accordance with another aspect of the disclosed subject matter, a method of performing sclerotherapy on a blood vessel, e.g. a varicose vein or hemorrhoid, is disclosed which includes advancing a guidewire catheter into the blood vessel to be occluded, wherein a portion of the guidewire catheter is surrounded by a slidable concentric tube disposed thereupon. The slidable concentric tube is coupled to at least two occlusion elements configured for conversion between an unexpanded and expanded position. The slidable concentric tube also contains at least one port disposed between the at least two occlusion elements. In operation, sliding the concentric tube in a first, e.g. distal, direction to cause the at least two occlusion elements to expand and occlude a portion of the blood vessel. Thereafter, a sclerosing agent is dispensed through a space between the guidewire catheter and the concentric tube, such that the portion of the blood vessel proximal of the first occlusion element is exposed to the sclerosing agent.

Additionally, the method of sclerotherapy disclosed can include reaspirating the sclerosing agent from the occluded vessel, and sliding the concentric tube in a second, e.g. proximal, direction to cause the at least two occlusion elements to collapse and removing the guidewire catheter from the blood vessel. Optionally, the blood vessels can also be compressed with bandages to expedite the procedure. In some embodiments the occlusion elements expand and contract solely via mechanical forces.

It is to be understood that both the foregoing general description and the following detailed description are exemplary and are intended to provide further explanation of the disclosed subject matter.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIG. 1 is a schematic view of a catheter embodying two inflatable balloons;

FIG. 2 is a cross-sectional views of the catheter of FIG. 1, taken along line A-A;

DETAILED DESCRIPTION OF EXEMPLARY EMBODIMENTS

Figure 3:
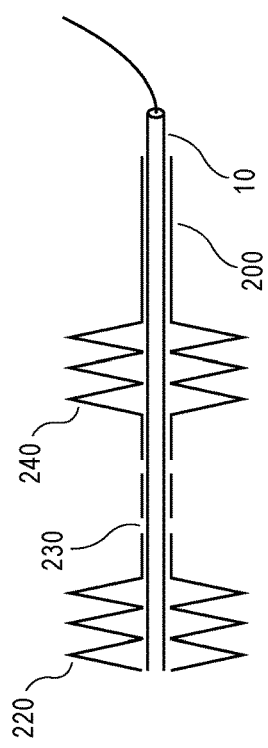
FIG. 3 illustrates a schematic view of the occluding apparatus depicting first and second expandable members in an expanded configuration.

It is understood that the subject matter described herein is not limited to particular embodiments described, and as such may, of course, vary. It is also understood that the terminology used herein is for the purpose of describing particular embodiments only, and is not intended to be limiting, since the scope of the present subject matter is limited only by the appended claims.

FIG. 1 depicts a conventional dual balloon catheter having two spaced-apart balloons, e.g., the occlusion balloon 40 and dilatation/occlusion balloon 50, as disclosed in U.S. Pat. No. 7,060,051, the entirety of which is hereby incorporated by reference. The outer catheter 10 is configured with two lumina (not shown). The catheter can include a distal orifice 90, a metal marker 120 to enable x-ray identification of the location of the dilatation/occlusion balloon, and a catheter segment 20 that connects the two balloons. Extending through the orifice 90, a guidewire 34 has a stop plug 170 which can be used to cap the orifice 90. A plurality of ports or holes 70 extend through the wall of the catheter segment 20 which permits a biologically active agent to pass from an inner lumen in the catheter segment 20 to the exterior of the catheter segment 20 and thereby target treatment to the section of the body lumen between the two balloons or the occluded portion of the body lumen. The inflatable balloons of such conventional designs require a pressure source to deliver inflation medium, e.g. fluid, at elevated pressures to pneumatically or hydraulically expand the balloons. Accordingly, and as shown in FIG. 1 a plurality of Y connectors, 140 and 160 with side ports 130 and 150 are required with connections 100 and 110 for supplying the pressurizing medium.

FIG. 2 shows an exemplary embodiment of a cross-sectional view of the catheter of FIG. 1 at section A-A. The outer catheter is shown with two lumens 35 and 33. An inner catheter stem 31 is shown inserted into lumen 33 and this stem 31 has two lumens 30 and 32. This view shows that four different lumens are required to provide independent pressure control to occlusion balloon 40 and balloon 50, to deliver a biologically active agent through the holes 70, and to receive the guidewire 34. The outer catheter 10 is configured with two lumina. The lumen 35 serves to supply the pressurizing medium to the occlusion balloon 40 while the lumen 33 permits a biologically active agent to be delivered to a targeted vessel portion. The lumen 30 serves to supply the pressurizing medium to dilatation/occlusion balloon 50 while lumen 32 can be used to receive guidewire 34. Consequently, such conventional dual balloon catheter designs require a complex catheter construction including at least three separate channels within the catheter to service the two balloons and to deliver the therapeutic agents through the catheter holes 70. Such conventional devices can present numerous manufacturing challenges.

The device and methods of the presently disclosed subject matter do not require the complexities of the conventional dual balloon embodiment, and thus alleviate the burdens of such intricate catheter designs with distinct lumens and connections to external pressurized fluid sources. Examples of such conventional dual balloon occlusion catheters are described in U.S. Pat. Nos. 7,077,836; 6,997,898 and 5,665,063, each of which is hereby incorporated by reference in their entirety.

Figure 4:
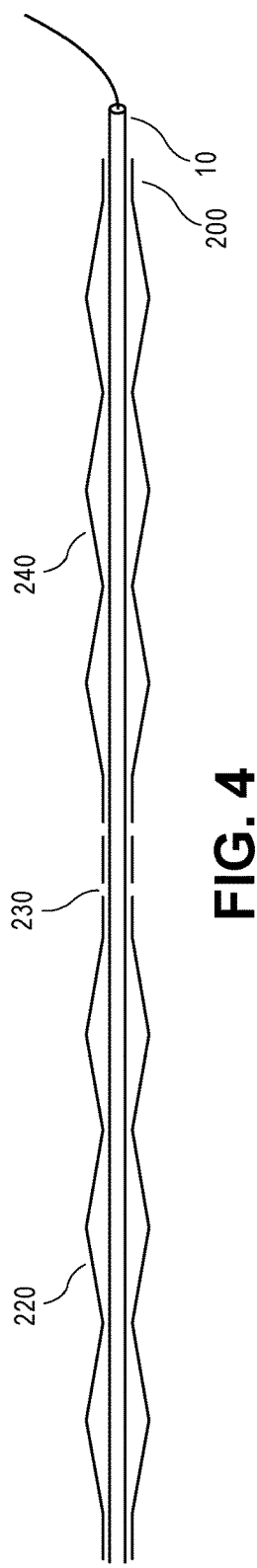
FIG. 4 illustrates a schematic view of the occluding apparatus depicting first and second expandable members in an collapsed configuration.

Instead, and in accordance with an aspect of the presently disclosed subject matter, a sleeve or sheath 200 which is configured as a concentric tube is coupled to the catheter 10 in slideable fashion such that the sleeve 200 can move proximally and distally along a length of the catheter 10. The concentric tube 200 includes a plurality of bellows 220, 240 coupled thereto which can convert between expanded (as shown in FIG. 3) and unexpanded or collapsed configurations (as shown in FIG. 4). The concentric tube 200 includes a mechanism (not shown) which extends to the proximal end of the catheter to allow for a physician to slide the concentric tube 200 proximally and distally to thereby contract and expand the bellows 220, 240. Preferably, the catheter 10 is advanced in the body lumen with the expandable members, i.e. bellows 220, 240 in the collapsed or unexpanded configuration. This is advantageous in that the reduced profile of the collapsed bellows 220, 240 eliminate or reduce the occurrence of friction or tearing along the inner wall of the blood vessel.

Once the catheter reaches the desired location, the concentric tube 200 can be displaced in the proximal and distal directions with respect to the catheter. The concentric tube 200 is connected via a mechanical linkage to the bellows 220, 240. Accordingly, as the concentric tube 200 is advanced in a distal direction the bellows 220, 240 expand to occlude the blood vessel.

The direct mechanical linkage between the concentric tube 200 and bellows 220, 240 provides the physician with controlled expansion/contraction based on gradual sliding of tube 200. For example, ratio of movement between the tube 200 and bellows 220, 240 can be 1:1 such that one unit, e.g. cm, of displacement results in one unit of expansion/contraction of the bellows, though alternative ratios are contemplated to be within the scope of the present disclosure. Additionally, the physician can choose a slow constant expansion/contraction rate or abruptly expand/contract the bellows by sliding the tube 200 accordingly. Furthermore, in some embodiments each bellow 220 and 240 can expand at the same rate and to the same degree via solely mechanical forces (i.e. no hydraulic or pneumatic pressure is required). Additionally, or alternatively, the bellows 220, 240 can be configured to expand at different rates and/or to different degrees.

Additionally, the expandable bellows 220, 240 can be designed to expand to any diameter as so desired, thereby accommodating a wide range of vessel sizes in a single design. For example, each bellows 220, 240 may include several sequentially arranged undulations, and pairs of undulations in the sequence may be joined at respective edges. Thus, a length of an undulation between sequential edges may determine a diameter to which the undulation is able to expand. The undulations may be continuously arranged with no intervening tubular segments such that adjacent undulations extend obliquely from a respective edge relative to a central axis of the catheter 10. More particularly, the undulations may be continuously joined at sequential edges such that a cross-sectional profile of the undulations of each bellows 220, 240 includes a zig-zag profile having lines joined at respective inner and/or outer vertices as shown in FIGS. 3-4. The relative positioning, i.e., distance between bellows 220, 240 can also be selected as so desired to occlude any predetermined length of a blood vessel.

The concentric tube 200 is disposed on the catheter in such a manner that an annular space or lumen is defined between the outer surface of the catheter 10 and the inner surface of the concentric tube 200. During the medical treatment a therapeutic agent is delivered through this lumen and dispenses into the vessel via ports 230 disposed between the bellows 220, 240.

These ports 230 can be arranged in a uniform pattern along the length of the concentric tube 200, or alternatively, be configured in a predetermined varied density pattern such that the tube 200 exhibits a varied dispensing/concentration. For example, the tube 200 can be configured with a greater number of ports 230 at one end to provide for a higher concentration of agent delivered to localized areas of the vessel wall. Accordingly, it will be obvious to one of ordinary skill that the number and location of the ports 230 can be varied to distribute the therapeutic agent within the occluded vessel section in any manner as so desired.

Upon dispensing, the therapeutic agent interacts with the inner walls of the occluded portion of the blood vessel to provide the desired medical treatment, such as sclerotherapy. Additionally, after the desired amount of therapeutic agent is dispensed into the vessel and the inner walls of the blood vessel have been exposed to the agent for a predetermined time to achieve the desired efficacy, the therapeutic agent can be re-aspirated out of the occluded section of the vessel. This is achieved by withdrawing the therapeutic agent from vessel through ports 230.

Upon completion of the sclerotherapy treatment, the concentric tube 200 is displaced in a proximal direction. This proximal displacement of tube 200 engages the mechanical linkage coupled to the bellows to cause contraction or collapse of the bellows 220, 240. As described above with respect to expansion, in some embodiments each bellow 220 and 240 can contract at the same rate and to the same degree via solely mechanical forces (i.e. no hydraulic or pneumatic pressure is required). This is advantageous in that it ensures proper and complete collapse of the bellows, thereby minimizing risk of damage to the inner wall of the blood vessel. Additionally, or alternatively, the bellows 220, 240 can be configured to collapse at different rates and/or to different degrees. While the direction of tube displacement described above indicates that distal movement of the tube causes expansion and proximal displacement of the tube causes contraction, it is to be understood that this orientation can be reversed if so desired.

For purpose of illustration and not limitation, Sclerosing agents compatible with the present invention include, but are not limited to, alcohols such as ethanol or polidocanol (POL), as well as sodium tetradecyl sulphate (STS), Sclerodex, hypertonic saline, glycerin and chromated glycerin, or combinations thereof. These sclerosing agents have been found to effect the cellular responses to growth stimulation and cause the vessel walls to immediately shrink upon exposure to the agents. While specific examples of sclerosing agents are described herein, it is to be understood that alternative therapeutic agents can be administered to the vessel wall utilizing the device and methods disclosed herein. Accordingly, as used herein, a "therapeutic agent" includes any agent that promotes health, recovery or diagnosis. For example, the therapeutic agent may be a drug, protein, or contrast agent.

Figure 5:
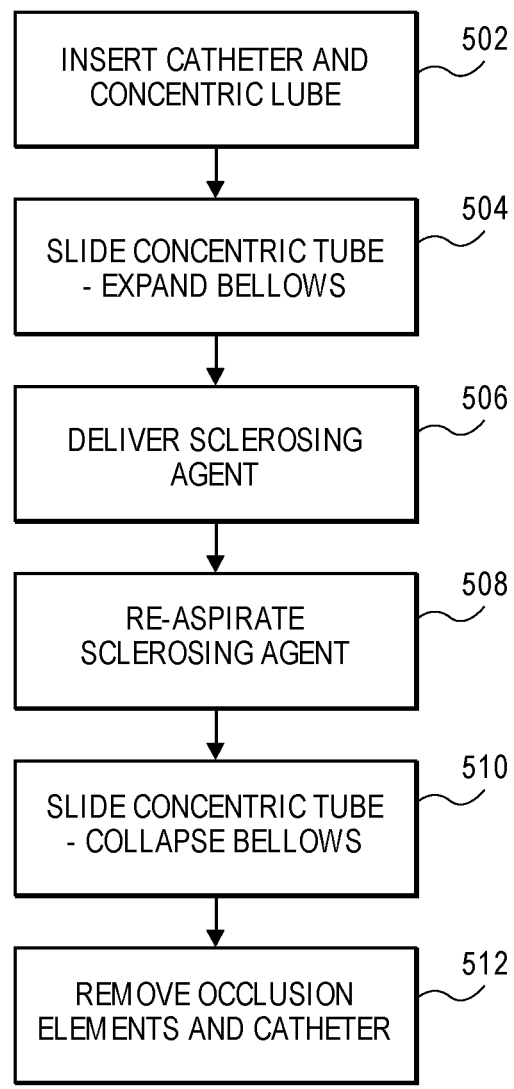
FIG. 5 illustrates a flow chart of the various steps of the system disclosed herein.

A method of performing sclerotherapy in accordance with the presently described subject matter is also included herein. Now, with reference to FIG. 5, a flowchart is provided illustrating steps for performing sclerotherapy using the different embodiments of the device described herein. First, the catheter is inserted into the blood vessel to deliver the concentric tube to the desired location at 502. Next, the concentric tube is advanced in a distal direction to expand the bellows at 504. The space between the occlusion elements, i.e. bellows, in the blood vessel defines the region for performing sclerotherapy. The sclerosing agent is then delivered through the ports of the concentric tube at 506. After the sclerosing agent has been imparted to the walls of the blood vessel, the sclerosing agent is removed or re-aspirated from the blood vessel at 508. The concentric tube is then retraced in a proximal direction to collapse the bellows at 510. Thereafter, the occlusion elements (i.e. concentric tube and bellows) and catheter are withdrawn from the vessel. Additionally, in some sclerotherapy treatments, the patient's blood vessels can be compressed via external bandages to facilitate the efficacy of the treatment and expedite the procedure.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. An apparatus for occluding a blood vessel, comprising:
    a catheter having a catheter body and a guidewire lumen extending along a central axis of the catheter body;
    a first bellows over the catheter body, wherein the first bellows includes a first end and a second end, and a plurality of first v-shaped undulations joined at a first vertex between the first end and the second end, wherein the first v-shaped undulations extend obliquely from the first vertex relative to the central axis to form a first angle between the first v-shaped undulations, and wherein the first bellows is configured for conversion between an unexpanded configuration and an expanded configuration;
    a second bellows over the catheter body and proximal to the first bellows, wherein the second bellows includes a third end and a fourth end, and a plurality of second v-shaped undulations joined at a second vertex between the third end and the fourth end, wherein the second v-shaped undulations extend obliquely from the second vertex relative to the central axis to form a second angle between the second v-shaped undulations, and wherein the second bellows is configured for conversion between an unexpanded configuration and an expanded configuration; and
    a concentric tube slidably disposed over the catheter body, wherein the concentric tube is attached to the first end of the first bellows and the third end of the second bellows to define a region radially outward of the concentric tube between the first bellows and the second bellows, and wherein the concentric tube contains a port between the region and the catheter body;
    wherein an axial displacement of the concentric tube by a first distance relative to the catheter body results in a radial expansion of the first bellows and the second bellows by a second distance relative to the catheter body, wherein the second distance is equal to the first distance times a constant ratio, and wherein the first bellows and the second bellows simultaneously expand by the same second distance to an expanded diameter to occlude the blood vessel for delivery of a therapeutic agent through the port into the region.

2. The apparatus of claim 1, wherein the first bellows and the second bellows are part of three or more bellows coupled to the concentric tube.

3. The apparatus of claim 2, wherein the therapeutic agent is a sclerosing agent.

4. The apparatus of claim 3, wherein the sclerosing agent is ethanol.

5. The apparatus of claim 2, wherein the therapeutic agent is delivered in a lumen defined in a space between the concentric tube and the catheter body.

6. The apparatus of claim 2, wherein the port is disposed between the first bellows and the second bellows.

7. The apparatus of claim 1, wherein the first bellows and the second bellows expand at equivalent rates when the concentric tube is axially displaced relative to the catheter body.

8. The apparatus of claim 1, wherein the first bellows and the second bellows expand or contract via mechanical forces.

9. The apparatus of claim 1, wherein the axial displacement is in a first direction, and wherein a second axial displacement of the concentric tube in a second direction relative to the catheter body results in a radial contraction of the first bellow and the second bellows.

10. The apparatus of claim 9, wherein the first direction is distal and the second direction is proximal.

11. A method of performing sclerotherapy on a blood vessel comprising:
    advancing a guidewire catheter having a catheter body and a guidewire lumen extending along a central axis of the catheter body into the blood vessel to be occluded;
    wherein a portion of the guidewire catheter is surrounded by a slidable concentric tube disposed thereupon; and
    wherein the slidable concentric tube is attached to a first bellows and a second at bellows to define a region radially outward of the concentric tube between the first bellows and the second bellows to be disposed over the catheter body, wherein each bellows includes a first end, a second end, and a plurality of v-shaped undulations joined at a vertex between the first end and second end, wherein the v-shaped undulations extend obliquely from the vertex relative to the central axis to form an angle between the v-shaped undulations, and wherein the bellows are configured for conversion between an unexpanded diameter in an unexpanded configuration to an expanded diameter in an expanded configuration; and
    wherein the slidable concentric tube is connected to respective first ends of the first bellows and the second bellows and contains a port disposed between the region and the catheter body;
    sliding the concentric tube in a first-direction by a first distance relative to the catheter body to cause the first bellows and the second bellows to radially expand by a second distance relative to the catheter body, wherein the second distance is equal to the first distance times a constant ratio, and wherein the first bellows and the second bellows simultaneously expand by the same second distance to the expanded diameter to occlude the blood vessel, the at least two bellows expanding via mechanical forces at equivalent rates;
    dispensing a sclerosing agent through a space between the guidewire catheter and the concentric tube and through the port into the region, such that the portion of the blood vessel between the first bellows and the second bellows is exposed to the sclerosing agent;
reaspirating the sclerosing agent from the occluded vessel;
sliding the concentric tube in a second-direction to cause the first bellows and the second bellows to collapse;
removing the guidewire catheter from the blood vessel; and compressing the blood vessel with bandages.

* * * * *